(12) United States Patent
Boudier et al.

(10) Patent No.: US 8,536,537 B2
(45) Date of Patent: Sep. 17, 2013

(54) ADJUSTABLE MEDICAL IMAGING DEVICE

(75) Inventors: Aurelie Boudier, Buc (FR); Serge Muller, Buc (FR)

(73) Assignee: General Electric Company, Schenectady, NY (US)

( * ) Notice: Subject to any disclaimer, the term of this patent is extended or adjusted under 35 U.S.C. 154(b) by 247 days.

(21) Appl. No.: 13/049,027

(22) Filed: Mar. 16, 2011

(65) Prior Publication Data

US 2011/0226959 A1   Sep. 22, 2011

(30) Foreign Application Priority Data

Mar. 17, 2010 (FR) ...................................... 10 51887

(51) Int. Cl.
*G01J 1/04* (2006.01)
(52) U.S. Cl.
USPC ........................................................ 250/393
(58) Field of Classification Search
USPC ............ 250/363.01, 363.02, 370.08, 370.09, 250/393; 378/37
See application file for complete search history.

(56) References Cited

U.S. PATENT DOCUMENTS

| 7,327,825 B2 | 2/2008 | Roncaglioni et al. |
| 2007/0237309 A1 | 10/2007 | Marinelli et al. |
| 2008/0181360 A1 * | 7/2008 | Hemmendorff ................ 378/37 |
| 2009/0003520 A1 | 1/2009 | Kanemitsu et al. |
| 2009/0086928 A1 | 4/2009 | Nakata et al. |

FOREIGN PATENT DOCUMENTS

| DE | 102006048607 A1 | 4/2008 |
| DE | 102008006115 A1 | 7/2009 |

OTHER PUBLICATIONS

102006048607 DE English Language Translation, Apr. 17, 2008.
102008006115 DE English Language Translation, Jul. 30, 2009.

* cited by examiner

*Primary Examiner* — Mark R Gaworecki
(74) *Attorney, Agent, or Firm* — Global Patent Operation; Marc A. Vivenzio

(57) ABSTRACT

A medical imaging device is provided. The medical imaging device includes an object support; a handle; a radiation source configured to emit radiation from a plurality of positions about the object support, wherein the positions are located substantially in a plane; a radiation detector configured to detect the radiation emitted by the radiation source; and displacement means configured to shift the handle relative to the radiation detector and to the radiation source.

8 Claims, 1 Drawing Sheet

ADJUSTABLE MEDICAL IMAGING DEVICE

FIELD OF INVENTION

The field of the invention relates generally to medical imaging, and more particularly to a medical imaging device for mammography.

BACKGROUND OF THE INVENTION

Tomosynthesis is a variant of conventional planar tomography in which a limited number of radiographic projections of an organ of a patient is acquired in digital form at different angles relative to the patient. The set of projections acquired at different angles is then processed to produce 3D information of the organ of the patient. This 3D information can be displayed according to a set of sectional planes or in any other form of 3D representation.

Mammography devices via tomosynthesis known to date comprise an arm bearing a radiation source capable of emitting radiation, a radiation detector capable of receiving the radiation, a planar object support placed between the source and the detector, one or more handles located on either side of a plane passing through the source and the detector, a plate placed between the object support and the source for compression of the object to be imaged and the processing means. The arm bearing the source is capable of being moved into a plurality of positions. This arm plays the role of positioner. The source is as such mounted pivoting on the arm to enable orientation of the latter relative to the object support. These devices enable acquisition of radiographic projections of the breast of the patient for different angles during a sequence of exposures to radiation.

The dimensions of the devices of the prior art are provided optimal for a patient having criteria morphological means established statistically, for example.

However, few patients satisfy these morphological criteria means such that use of such apparatus is a source discomfort for the patient. In fact, leg or arm length (and more generally size) can vary from one patient to another.

Embodiments of the present invention provide an ergonomic medical imaging device which is more comfortable for patients.

SUMMARY OF THE INVENTION

For this purpose, a medical imaging device is provided. The medical imaging device comprises: an object support; a handle intended to be gripped by a patient; a radiation source for emitting radiation from a plurality of positions about the object support, said positions being located substantially in one plane; and a radiation detector capable of detecting the radiation emitted by the source. The device further comprises means adapted for shifting the handle relative to the radiation detector and to the radiation source.

Another embodiment of the present invention relates to an imaging method for an imaging device comprising an object support; a handle intended to be gripped by a patient; a radiation source configured to emit radiation from a plurality of positions about the object support; and a radiation detector configured to detect the radiation emitted by the radiation source; wherein the method comprises shifting a handle relative to the radiation detector and to the radiation source.

Another embodiment of the present invention relates to a computer program product comprising programmed code instructions for executing the method described hereinabove.

BRIEF DESCRIPTION OF THE DRAWINGS

Other characteristics and advantages of the device and of the method according to embodiments of the invention will emerge from the following description, which is purely illustrative and non-limiting and must be considered in reference to the attached diagrams, in which.

DETAILED DESCRIPTION OF THE INVENTION

Figure 1:
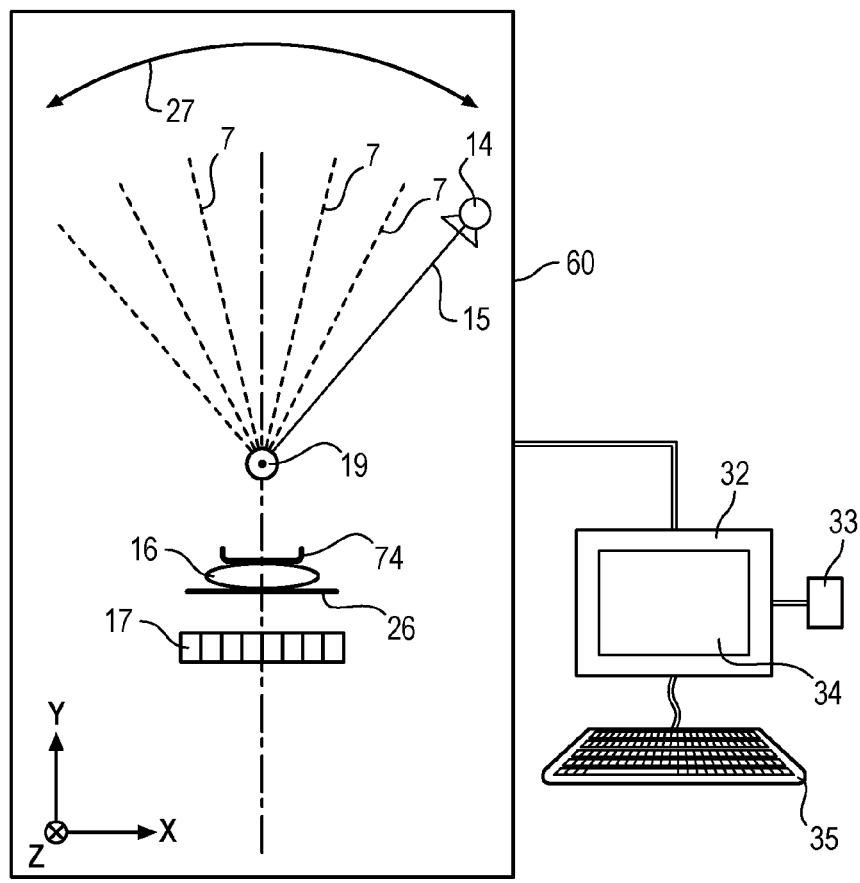
FIG. 1 is a schematic representation of a medical imaging device according to one embodiment of the present invention.

FIG. 1 represents a medical imaging assembly 13.

This ensemble 13 comprises a radiation source 14, a mobile arm 15, an object support 26, a radiation detector 17, control means, processing means 32, and a pad 74 placed between the object support 26 and the source 14 for compression of an object 16 to be imaged.

The mobile arm 15 is capable of being moved about a first axis 19 during a sequence of exposures to radiation. The arm 15 plays the role of positioner. Between each exposure to radiation of the sequence of exposures, the arm 15 is moved to enable acquisition of a radiographic projection of the imaged object 16 for a different angle. The arm 15 bears the radiation source 14 at one of its ends.

The radiation source 14 is capable of emitting radiation. The radiation source 14 is for example an X-ray source. The source can be shifted by the arm overall in a plane 60 (hereinafter called "displacement plane of the source") during an exposure sequence.

The object support 26 is capable of receiving the object 16 to be imaged. For example, in the case of mammography, the object 16 is the breast of a patient. The object support 26 is for example a plate. The object support 26 is fixed during a sequence of exposures to radiation. However, the object support 26 can be shifted manually or automatically between two sequences of exposures, especially to adapt the height of the object support as a function of the size of the patient, or for transitioning from one acquisition mode to another. For example, if the user has just completed reconstruction of 3D information in a cranio-caudal view (CC), and wants to obtain 3D information in a medio-lateral oblique view (MLO), the user can control the pivoting of the object support 26 to place it in an oblique plane relative to a vertical plane, the object support and the other elements of the device (i.e. arm mobile, radiation source, radiation detector, etc.) being shifted firmly to shift from CC to MLO.

The radiation detector 17 is capable of detecting radiation emitted by the radiation source 14. The radiation detector 17 is for example a planar sensor or an image amplifier linked to a camera. The radiation detector 17 can be substantially planar or be curved.

The radiation detector 17 can be mobile during the sequence of exposures. In this case, the detector 17 is shifted between two exposures to radiation of the sequence of exposures. The radiation detector 17 can also be fixed during a sequence of exposures to radiation. In this case however, the radiation detector 17 can be shifted in translation or shifted in rotation between two sequences of exposures, as can the object support 26, especially to adapt the height of the detector to the size of the patient or for moving for example from a CC acquisition mode to an MLO acquisition mode.

The device also comprises one or more handle(s) 1 intended to be gripped by the patient during a sequence of exposures. Hereinbelow, it is assumed that the imaging device comprises a handle, given for the expert that the device can comprise a plurality of handles.

Advantageously, the device comprises displacement means adapted for shifting the handle 1 relative to the radiation detector 17 and to the radiation source 14.

This allows an imaging device according to embodiments of the invention to adapt to the morphology of the patient. In a variant, the displacement means is adapted to vary the depth z of the handle 1 such that it can be moved closer to or moved away from of the patient.

This adapts the distance between the handle 1 and the patient as a function of its size. The displacement means can comprise a throat 2 whereof the form is complementary to that of the handle 1 to allow the latter to slide inside the throat 2 between a neutral position and a deployed position.

Figure 2:
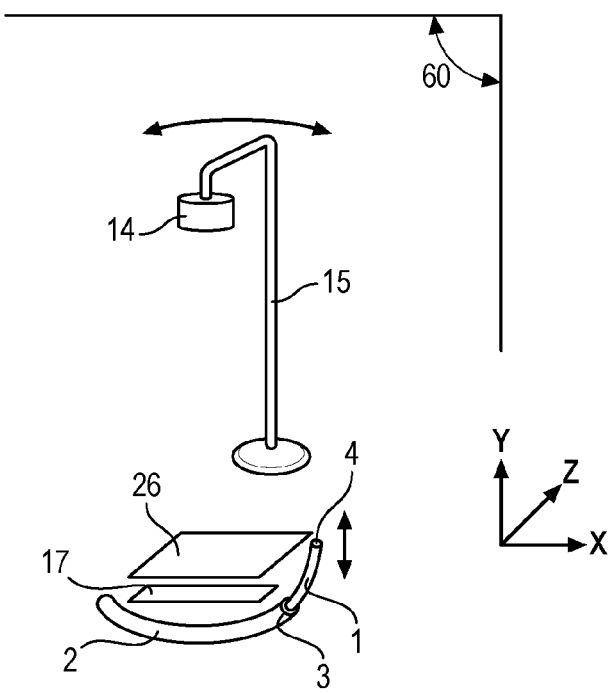
FIG. 2 is a schematic representation of a medical imaging device according to one embodiment of the present invention.

For example in an embodiment illustrated in FIG. 2, the handle 1 is a U-shaped tube. The throat 2 also has a U-shape of diameter greater than the diameter of the handle 1 such that it can slide inside the throat 2.

The U-shaped throat 2 is located under the object support 26 such that the object support 26 is positioned between the throat 2 and the radiation source 14. The throat 2 comprises at least one open end 3 for passage of the handle 1. This open end is oriented upwards. In other words, the open end 3 of the throat 2 is opposite the radiation source 14.

In the embodiment illustrated in FIG. 2, the open end 3 is inclined relative to the vertical in a direction opposite the patient such that the free end 4 of the handle 1 is closer to the patient in the neutral position than in the deployed position.

This particular arrangement of the throat 2 adapts the depth of the handle 1 to the size of the patient. The greater the size of the patient, the more the handle 1 deploys such that the free end 4 moves away from the patient to adapt to the length of her arms, while moving upwards. Inversely, the smaller the size of the patient, the more the handle 1 is stowed such that the free end 4 moves closer to the patient to adapt to the length of her arms, while moving downwards.

The adjustment in depth of the handle 1 is for example a function of the height y of the object support 26 which depends on the size of the patient.

In fact, the length of the arms of a large person is greater than the length of the arms of a small person.

When the object support 26 is shifted upwards the handle is shifted towards the rear such that the handle 1 moves away from the patient, for a large patient for example. When the object support 26 is shifted downwards, the handle 1 is shifted forwards such that the handle 1 moves closer to the patient.

In another variant, the displacement means is adapted for shifting the handle 1 in a vertical plane parallel to the plane of displacement of the source 14.

This adapts the position of the handle as a function of the acquisition mode—CC or MLO—to be carried out.

In the cranio-caudal (CC) acquisition mode, the object support 26 extends in a substantially horizontal plane. The displacement means position the handle 1 to the side of the object support such that it extends perpendicularly to the object support 26.

In the medio-lateral oblique acquisition mode (MLO), the object support 26 extends in an oblique plane relative to a vertical plane. The displacement means position the handle 1 above the object support 26 such that it extends perpendicularly to the object support 26.

This makes the imaging device more comfortable for the patient. In fact, the fact that the handle 1 is always perpendicular to the object support 26 irrespective of the acquisition mode allows the patient gripping the handle to be in a more natural position.

Also, the combination of the handle and the displacement means plays the role of positioning means. The handle is shifted to the location where the user wants the patient to put her hand, thus making acquisition easier by limiting the number of explanations necessary for the patient to be positioned correctly during acquisition.

Displacement of the handle can be manual. In this case, displacement can be done either by the user, or by the patient herself for adapting the position of the handle to the morphology of the patient and/or to the preferred acquisition mode (CC or MLO).

The displacement of the handle can also be automatic. In this case, displacement of the handle is initiated or not by displacement of the object support.

In an embodiment, the handle and the object support are connected to independent drive means such as motors. Displacement of the handle is synchronised with displacement of the object support due to a law of displacement executed in software.

For example, the object support is shifted upwards or downwards to a use position. The coordinates of the use position are detected using detection means such as an optic sensor. The detection means transmits to processing means—such as a computer—the coordinates of the use position of the object support.

The processing means utilizes a conversion table (or "look up table" in English terminology) stored in memory providing the use position of the handle as a function of the position of the object support. The use position of the object support is used at input of the conversion table, which provides at output the use position of the handle. The handle is then shifted by the drive means to its use position.

In another embodiment, the handle is connected by mechanical means to the object support such that displacement of the handle is initiated by the object support. Displacement of the object support causes displacement of the handle.

In all cases of automatic displacement of the handle, removal means can be provided between the drive means or the mechanical means to allow manual displacement of the handle, especially in the case of a patient presenting a particular morphology (large person having short arms or small person having long arms).

The imaging device described hereinabove has numerous advantages, including improving patient comfort.

It better adapts the position of the handle as a function of the acquisition mode (CC, MLO) which the user wants and therefore improves ergonomics of the device. This has the advantage if increasing the workspace of the user during the acquisition procedure.

It will be evident that numerous modifications can be made without departing in material terms from novel ideas and the advantages described here.

For example, displacements of the handle in depth and in the displacement plane of the source can be combined or not.

Also, displacement of the handle can be independent of the position of the object support. For example, in an embodiment, the handle is shifted automatically by using a predefined algorithm which establishes a link between a view name and the position of the handle. The view name can be determined for example by using a method described in U.S. Pat. No. 6,687,331.

Consequently, all modifications of this type are intended to be incorporated inside the reach of the system and of the imaging method such as defined in the attached claims.

What is claimed is:

1. A medical imaging device, the device comprising:
an object support;

a handle;

a radiation source configured to emit radiation from a plurality of positions about the object support, wherein the positions are located substantially in a plane;

a radiation detector configured to detect the radiation emitted by the radiation source; and displacement means configured to shift the handle relative to the object support as a function of a position of the object support.

2. The device of claim 1, wherein the displacement means comprise a component perpendicular to the plane in which the positions are located.

3. The device of claim 1, wherein the displacement means comprise a component perpendicular to the object support.

4. The device of claim 1, wherein the displacement means automatically shift the handle as a function of the position of the object support.

5. The device of claim 4, wherein the displacement means shift the handle from an initial position to a final position, wherein the final position is determined by using a law of displacement executed by software.

6. The device of claim 4, wherein the displacement means comprise mechanical connection elements between the handle and the object support such that the handle is driven by the object support.

7. A medical imaging method for an imaging device, the imaging device comprising an object support; a handle; a radiation source configured to emit radiation from a plurality of positions about the object support; and a radiation detector configured to detect the radiation emitted by the radiation source, wherein the method comprises shifting the handle relative to the object support as a function of a position of the object support.

8. A medical imaging device, the device comprising:

an object support;

a handle;

a radiation source configured to emit radiation from a plurality of positions about the object support, wherein the positions are located substantially in a plane;

a radiation detector configured to detect the radiation emitted by the radiation source; and displacement means configured to shift the handle relative to the radiation detector and to the radiation source;

wherein the displacement means comprise a throat configured to receive the handle, into which the handle slides between a neutral position and a deployed position, wherein an end of the throat is inclined relative to the plane and extends towards the radiation source such that the handle can be moved closer to or moved away from a positioning zone of the patient.

* * * * *